United States Patent [19]

Satek

[11] Patent Number: 4,590,324

[45] Date of Patent: May 20, 1986

[54] DEHYDROGENATION OF ALKYLAROMATICS

[75] Inventor: Larry C. Satek, Wheaton, Ill.

[73] Assignee: Amoco Corporation, Chicago, Ill.

[21] Appl. No.: 710,043

[22] Filed: Mar. 11, 1985

[51] Int. Cl.$^4$ .............................................. C07C 2/64
[52] U.S. Cl. ................................................... 585/444
[58] Field of Search ....................................... 585/444

[56] References Cited

U.S. PATENT DOCUMENTS

| | | | |
|---|---|---|---|
| 3,856,702 | 12/1974 | McArthur | 502/202 |
| 3,856,705 | 12/1974 | McArthur | 502/202 |
| 4,024,171 | 5/1977 | McArthur | 502/207 |

*Primary Examiner*—Curtis R. Davis
*Attorney, Agent, or Firm*—William H. Magidson; William T. McClain; Ralph C. Medhurst

[57] ABSTRACT

A method of dehydrogenating an alkylaromatic compound containing at least two carbon atoms and at least one alkyl group to an alkenylaromatic which comprises contacting the alkylaromatic with a catalyst comprising copper on a support comprising aluminum borate.

12 Claims, No Drawings

DEHYDROGENATION OF ALKYLAROMATICS

This invention relates to the dehydrogenation of alkylaromatics containing at least two carbon atoms in at least one alkyl group to alkenylaromatics using a catalyst comprising metallic copper on a support comprising aluminum borate. More particularly, this invention relates to the dehydrogenation of ethylbenzene to styrene, cumene to alphamethylstyrene and paraethyltoluene to paramethylstyrene (vinyltoluene) with a catalyst comprising finely divided metallic copper on a support comprising aluminum borate.

Chu in U.S. Pat. No. 4,433,186 points out that styrene and styrene derivatives are typically produced from ethylbenzene materials by dehydrogenation over solid catalysts in the presence of co-fed steam at temperatures ranging from about 500°–700° C. Chu indicates that the most effective catalysts for this process are based on potassium oxide promoted, chromium stabilized, iron oxide materials. These catalysts are considered to be self-regenerative inasmuch as, in addition to their effectiveness in promoting dehydrogenation, they also promote the water gas reaction in the presence of the co-fed steam thereby removing coke which would otherwise build up and deactivate the catalyst.

Because of this ability to decoke themselves in the presence of steam, potassium doped iron oxide catalysts can be used to convert ethylbenzene and ethyltoluene to respectively styrene and vinyltoluene over a period of about 6 months without any additional regeneration of the catalyst. However, cumene conversion to alphamethylstyrene in the presence of steam generally requires a separate steam regeneration every three days during the first two or three months the iron oxide catalyst is on stream and then daily steam regeneration. Typically, these conversions run from about 40 to 60% with a selectivity of from about 80 to 90% under optimum conditions. While these processes of converting alkylaromatics to alkenylaromatics are commercially attractive, it is desirable to provide a new class of catalysts for dehydrogenation of alkylaromatics. Further, it is desirable to minimize or avoid the use of steam in the dehydrogenation process since steam is a significant operational cost. Accordingly, there is a need for a new process of producing alkenylaromatics.

Ethylbenzene and ethyltoluene are typically produced by the ethylene alkylation of benzene and toluene respectively. These alkylations are generally carried out to relatively low levels of conversion to avoid the diethylation of the starting material and subsequent production of divinyl monomers in the dehydrogenation reactions. While theoretically the presence of unreacted benzene and toluene would be advantageous in the dehydrogenation step in decreasing the contact time of the ethylaromatic with the dehydrogenation catalyst and thereby reducing coking, this can not be done unless the benzene or toluene are substantially inert to the catalyst. Unfortunately, both benzene and toluene coke up the conventional iron oxide catalysts and the toluene is dealkylated to an unacceptable degree. Accordingly, ethylbenzene and ethyltoluene are conventionally separated from benzene and toluene prior to dehydrogenation. For example, in the synthesis of vinyltoluene, attempts to feed typical 8:1 ratios of toluene to ethyltoluene to the dehydrogenation units results in unacceptable levels of dealkylation of the toluene diluent. Attempts to use $C_8$ refinery streams comprising about 20% ethylbenzene and 80% xylenes have been unsuccessful since there is undue coking and dealkylation of the xylenes over the conventional iron oxide dehydrogenation catalysts even in the presence of steam. If the separation of ethyltoluene or ethylbenzene from alkylation unit streams or from refinery streams could be omitted, there would be a substantial advantage in dehydrogenation of the precursors to styrene and vinyltoluene.

Uhlig discloses the preparation of a green tetragonal solid copper aluminum borate having the formula $Cu_2Al_6B_4O_{17}$ in Diplomarkeit, Institute for Crystallagraphy, Aacken (October 1976) "Phasen—und Mischkristall—Bildung im $B_2O_3$ armeren Teil des Systems $Al_2O_3$-$CuO$-$B_2O_3$" "Formation of Phases and Mixed Crystals in that Part of the $Al_2O_3$-$CuO$-$B_2O_3$ System With a Low $B_2O_3$ Content" which is hereby incorporated by reference, by grinding together solid boron oxide, copper oxide and alumina, sealing the ground metal oxides in a platinum tube and heating same at 1000° C. over the heating period of 48 hours. Attempts to produce this copper aluminum borate by the indicated route yields well defined, dense crystalline particles which have an extremely low surface area.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate having the X-ray diffraction comprising $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, etc.

The general object of this invention is to provide a new process of converting alkylaromatics containing at least two carbon atoms in at least one alkyl group to alkenylaromatics. Other objects appear hereinafter.

I have now found that the objects of this invention can be attained by the dehydrogenation of alkylaromatics containing at least two carbon atoms in at least one alkyl group to alkenylaromatics by contacting the alkylaromatics with a catalyst comprising copper on a support comprising aluminum borate. Surprisingly, I have found that these catalysts are very effective in converting alkylaromatics to alkenylaromatics without any need for co-fed steam or with reduced levels of steam and that it is possible to obtain conversions and selectivities comparable to those obtained with commercial dehydrogenation catalysts. The process of this invention is particularly useful for the conversion of cumene to alphamethylstyrene since it is possible to carry out this dehydrogenation for extended periods of time without any separate need for steam regeneration of the catalyst. Further, by proper selection of catalyst adjuncts, it is possible to use nitrogen, steam, alkanes, benzene or toluene as a diluent for the alkylaromatic. Accordingly, it is not necessary to separate benzene or toluene from ethylaromatics going to the dehydrogenation units.

Briefly, the process of this invention comprises contacting the alkylaromatic at a temperature of about 400° to 700° C. with a catalyst comprising copper on a support comprising aluminum borate. The catalyst charged to the reactor preferably comprises either copper aluminum borate or finely divided copper on a support comprising aluminum borate. If the catalyst charged to the reactor is copper aluminum borate, it can be reduced therein to finely divided copper on the support comprising aluminum borate with a reducing gas or with hydrogen coming off the alkylaromatic. Over a period of time, it is not unusual for substantially all of the copper in the copper aluminum borate to be reduced to copper metal with the result that the catalyst is primarily finely divided, zero valent copper on an aluminum borate support substantially free of copper aluminum borate.

The alkylaromatics useful in this invention include ethylbenzene, o, m, p-ethyltoluene and mixtures thereof; o, m, p-ethyl halobenzene (chlorobenzene, bromobenzene, etc.); cumene; o, m, p-diethylbenzene; p-cymene; ethylpyridine; etc. Of these, the preferred alkylaromatics are ethylbenzene, p-ethyltoluene and cumene.

The catalysts useful in this invention comprise zero valent copper on a support comprising aluminum borate. While these catalysts can be prepared by any method (e.g., by vapor phase deposition of metallic copper on an aluminum borate support) the preferred catalysts are produced by the reduction of copper in crystalline copper aluminum borate. The preferred copper aluminum borates are disclosed and claimed in application Ser. No. 709,790 filed Mar. 11, 1985 filed on even date in the name of Zletz, which is hereby incorporated by reference and zero valent copper on aluminum borate support, which is disclosed and claimed in Zletz commonly assigned application Serial No. 710,015 filed Mar. 11, 1985 which is hereby incorporated by reference.

If neat copper aluminum borate having the empirical formula $Cu_2Al_6B_4O_{17}$ is viewed as having the structure $3Al_2O_3.2CuO.2B_2O_3$, the reduction with CO or $H_2$ can be represented in its simplest terms as follows:

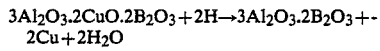

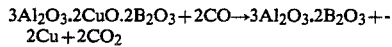

X-ray diffraction patterns of the products indicate that the aluminum borate crystal has the formula $2Al_2O_3.B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB, aluminum borate and copper. The X-ray diffraction patterns in Table I show the significant lines for unreduced CuAB, substantially fully reduced CuAB (copper on aluminum borate), $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these, the relative intensities, 100 $I/I_O$, where $I_O$ is the intensity of the strongest line or peak, and d (obs.), the interplanar spacing in A, corresponding to the recorded lines, were calculated. In Table I, the relative intensities are given in terms of the symbols VVS=very very strong (over 100), VS=very strong (80–100), S=strong (50–80), M=Medium (20–50), W=weak (10–20) and VW=very weak (<10).

TABLE I

| dA | Cu on AB | Cu AB | Uhlig Cu AB | $Al_4B_2O_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the $Al_4B_2O_9$ or copper.

The significant X-ray diffraction lines for copper aluminum borate are set forth below in Table A.

TABLE A

| dA | Strength |
|---|---|
| 5.29 ± 05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

The preferred copper aluminum borate precursors of copper on aluminum borate have the formula $CU_{2-x}Al_{6-y}B_4O_{17}M_mM'_nM''_y$ wherein M is a divalent metal, M' is a monovalent metal, m ranges from 0 to 0.8, n ranges from 0 to 1.6, X ranges from 0 to 0.8 and is equal to the sum of m+n/2, M" is a trivalent metal and y ranges from 0 to 1.2.

Briefly, the preferred copper aluminum borates useful in this invention are preferably prepared by a three step procedure which comprises (1) combining a source of divalent copper trivalent aluminum and boron in the in the form of the oxide or borate, (2) drying the composition to remove water or diluent if necessary and (3)

calcining the composition at a temperature sufficiently high to form crystalline copper aluminum borate.

While copper aluminum borate useful in this invention can be prepared by various techniques, it is generally preferred to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatized during the subsequent drying and/or calcination step. The presence of volatile components in preparation of copper aluminum borate, such as water, $NH_3$, acetate, etc., is advantageous in providing the copper aluminum borate with sufficient surface area and porosity for catalysis. Preferably, the catalyst has a surface area of at least 5 $m^2$/g. However, lower surface area copper aluminum borates can be used.

Accordingly, preferred sources of copper for use in this invention include copper nitrate, copper acetate, copper carbonate, copper borate, etc. since the nitrate, acetate and carbonate anions are destroyed during the drying or calcination step. Suitable sources of boron include boric acid, copper borate, aluminum borate, boron oxides and ammonium borate. The aluminum can be present in the form of alumina sols, aluminum nitrate, alumina, aluminum acetate, aluminum borate, etc. It is generally desirable to employ ammonium salts or ammonium hydroxide to increase the surface area and porosity of the copper aluminum borate. These components can be combined in an aqueous medium in approximately stoichiometric proportions to provide $Cu_2Al_6B_4O_{17}$. In some cases, it is desirable to have excess aluminum and borate present in the catalyst precursor in order to form a mixed copper aluminum borate/aluminum borate crystal.

If desired, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been incorporated into copper aluminum borate crystals and, accordingly, X in the above formula can range from about .01 to 0.8, preferably about 0.05 to 0.50. Trivalent metal ions can appear as M" in the above formula, e.g., $Fe^{+++}$. However, chromium forms a chromite and does not replace aluminum.

While it is generally preferred to produce neat copper aluminum borate or copper aluminum borate/aluminum borate catalysts, the partial replacement of aluminum with chromium (about 5 to 30%) yields an excellent dehydrogenation catalyst (copper aluminum borate/copper chromite) for conversion of alkylaromatics to alkenylaromatics. Dehydrogenation of cumene to α-methylstyrene over an 80% Cu/20% zinc aluminum borate gave a nearly colorless product compared with a slightly yellow color from CuAB. The preparation with copper chromite was even better than CuAB for dehydrogenating cumene, but showed dealkylation activity for p-cymene and p-ethyltoluene. The copper 90% Al-10% Fe borate gave lower conversion of cumene and p-ethyltoluene to the corresponding styrenes, but selectivities to dehydrogenated products were better than for CuAB. Likewise, conversion of ethylbenzene to styrene was lower than CuAB; catalytic activity did not deteriorate, whereas it does so rapidly with undoped CuAB.

If desired, non-volatile cations such as alkali metal (M' in the above formula) or alkaline earth metal cations can be present during the preparation of the copper aluminum borate.

In somewhat greater detail, the copper salt and boron compound are desirably dissolved in water together with a water soluble aluminum salt and/or alumina in the form of sols or powder. The composition is dried (e.g. at atmospheric pressure or under vacuum) and then calcined to a temperature of about 650° C. to 1000° C., preferably at least 800° C. for about 0.1 to 24 hours, typically in air. The higher the calcination temperature the shorter the calcination time. Calcination at about 680° C. for about 3 hours generally leads to about 20% crystallinity of copper aluminum borate, while calcination at about 845° C. for about 3 hours generally leads to about 80% crystallinity. Calcinations above about 800° C. tend to provide a blue-green crystalline material that is more active in dehydrogenation reactions than the green crystalline material obtained below about 800° C. Other things being equal, the higher the calcination temperature the lower the surface area and porosity of the copper aluminum borate. For example, copper aluminum borate calcined at 830° C. had a surface area of 19 $m^2$/g, pore volume of 0.1639 cc/g and an average pore radius of 293Å, whereas the same material calcined at 925° C. had a surface area of 7 $m^2$/g, pore volume of 0.0402 cc/g and an average pore radius of 334Å. Of course, the optimum calcination temperature is dependent on the particular composition calcined, the calcination time, the volatiles present during the preparation of the composition and the desired surface area and porosity.

The calcined copper aluminum borate can be used for dehydrogenation or treated with reducing gas, such as hydrogen or carbon monoxide at a temperature of from 150° C. to 1000° C. to convert same into catalysts having a surface area of at least 5 square meters per gram, comprising finely divided metallic copper on a support comprising aluminum borate. The higher the temperature of the reducing gas and the more effective the reducing gas, the lower the concentration of copper aluminum borate in the aluminum borate support. If the copper aluminum borate is used directly as a catalyst without pretreatment with a reducing gas, the copper aluminum borate can be converted into a catalyst having a surface area of at least 5 square meters per gram, comprising finely divided copper on a support comprising aluminum borate by the hydrogen formed in dehydrogenation of the alkylaromatic.

Either prior to or after the conversion of the copper aluminum borate to the catalyst comprising finely divided copper on a substrate or support comprising aluminum borate, the aluminum borate can be treated or doped with an alkali metal or alkaline earth metal compound for use in the dehydrogenation. Doping is particularly advantageous for conversion of ethylbenzene to styrene. This is the subject of copending application Ser. No. 711,235 in the name of Satek et al, filed on even date which is hereby incorporated by reference.

Suitable alkali metal and alkaline earth metal compounds include the oxides, hydroxides and salts of lithium, sodium, potassium, rubidium, cesium, magnesium, calcium, strontium, and barium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium, in the form of the oxide or in a form readily oxidizable to the oxide is preferred. The copper aluminum borate or copper on aluminum borate can be treated with from about 0.05 to 50 wt % dopant based on the weight of the copper aluminum borate or copper on aluminumborate. The alkali metal or alkaline earth metal compound can be dry blended with the copper aluminum borate or copper on aluminum borate; dissolved in a suitable solvent, preferably water, mixed with the copper aluminum borate or copper on aluminum borate and dried; or aqueous solutions of saome can be added to feedstocks going to a reactor containing the copper aluminum borate or copper on aluminum borate.

As indicated above, the preferred catalyst for dehydrogenation of the alkylaromatics varies to some extent with the particular hydrocarbon source. For example, present indications are that ethylbenzene cannot be converted to styrene in high yields and at high conversion with finely divided copper on an unmodified aluminum borate support. However, doping the support with alkali metal or alkaline earth-metal compound, particularly, a potassium compound, provides a catalyst capable of conversion of ethylbenzene to styrene at high conversion levels and high selectivity.

While substantially pure cumene can be converted to alphamethylstyrene in high yields and at high selectivity with finely-divided copper on an unmodified aluminum borate support, the presence of about 3% ethylbenzene in the cumene feed reduces the conversion and selectivity of the catalyst. However, by doping the support with alkali-metal or alkaline earth metal compound or by replacing part of the aluminum in the copper aluminum borate precursor with about 5 to 30% chromium on an atomic basis overcomes the inhibiting effect of ethylbenzene in the cumene feed.

Paraethyltoluene can be converted readily to paravinyltoluene with finely divided copper on an unmodified aluminum borate support. Cymene is readily converted to paramethylalphamethylstyrene with finely divided copper on an aluminum borate support without any additional need for modification of the catalyst. While the optimum catalyst for each individual feed varies, it is clear that copper on an aluminum borate support is an excellent catalyst for dehydrogenation of alkylaromatics to alkenylaromatics.

As indicated above, the copper aluminum borate can be reduced to finely divided copper on an aluminum borate support by treatment with a reducing agent or by treatment with hydrogen liberated during the dehydrogenation. However, these catalysts have the drawback that in some cases they reach maximum utility after an induction period. Typically, the catalyst selectivity increases from a relatively low level to maximum levels over a period of 2 to 3 days on stream. This conditioning of the catalyst can be avoided by treating the copper aluminum borate or copper on aluminum borate with dilute oxygen followed by a dilute reducing gas, preferably, carbon monoxide, before placing the unit on stream. This substantially eliminates the induction period for start up. This procedure can also be used for regeneration of the catalyst.

In somewhat greater detail, the process of this invention comprises the vapor phase dehydrogenation of alkylaromatics to alkenylaromatics. The alkylaromatic is fed under vapor phase conditions through a bed of the catalyst at a temperature of about 450° to 700° C.

As in many vapor phase processes, it is preferable to dilute the alkylaromatic to about 4 to 25 volume % alkylaromatic with a substantially inactive diluent compound which is gaseous under the reaction conditions. Inert gases, such as nitrogen, steam, alkanes of from 1 to 10 carbon atoms, benzene and toluene, can advantageously be used for this dilution. It should be noted that steam is not always an essential component but can be used as a diluent for the process and substantially the same results are obtained in the absence of alkali metal or alkaline earth metal compound whether the diluent is steam, nitrogen or the unreacted hydrocarbons. Oxygen should be avoided in the conversion of cymene since it has an inhibiting effect on the conversion of this alkylaromatic compound. The optimum gaseous diluent depends upon the particular alkylaromatic being treated and the availability of suitable diluents in the plant.

Alkali-metal or alkaline earth metal doping and steam are generally desirable when the alkylaromatic contains in excess of 1.5% to 2% by weight ethylbenzene. The copper or aluminum borate or copper aluminum borate can be doped prior to placing the catalyst in the reactor or dopant can be added to the alkylaromatic feed.

The gaseous stream of alkylaromatics can be passed over the catalyst or throughout the catalyst bed at a velocity from about 0.1 to 5 liquid hourly space velocity.

The alkenylaromatic products of this invention can be polymerized to various aromatic polymers as is conventional in this art.

EXAMPLE I

This Example illustrates that (1) substantially fully reduced copper aluminum borate (finely divided copper on aluminum borate support) has a different x-ray diffraction pattern from its unreduced precursors and (2) it is an excellent dehydrogenation catalyst for alkyl substituted aromatics having at least two carbon atoms in at least one alkyl group.

A hot solution of 23.16 g boric acid in 240 ml distilled water was added to 297.16 g of alumina sol (9.73 wt. % $Al_2O_3$ at 500° C.) in a Waring blender. To 37.35 g of copper acetate were added 100 ml distilled water and 30 ml conc. $NH_4OH$. This brought nearly all of the solid into solution and was added to the blender. An additional 30 ml conc. $NH_4OH$ was added to the small amount of remaining solid which was then transferred to the blender. One hundred ml distilled water was used to transfer all material to the blender. After each of these additions the mixture was thoroughly mixed and the final product was spread out to dry for eight days before drying in a vacuum oven to 90° C. This product (II-1) was then calcined at 820° C. for three hours and had a surface area of 54 m²/g, a pore volume of 0.2663 cc/g and an average pore radius of 92Å.

The copper aluminum borate was loaded into a ⅜" quartz reactor tube and placed in a Lindberg furnace. The reactor system was equipped with regulators for controlling nitrogen flow and a syringe pump for controlling liquid flows. The liquid was vaporized in a "preheat" section of the reactor and mixed with nitrogen before contacting the catalyst. The reactor effluent was fed into a 10 port gas sampling valve through heated lines. On a signal from the gas chromatograph, an 0.1 cc sample of the reactor effluent was injected into a Perkin-Elmer Sigma 2B Gas Chromatograph. A series of columns and splitters allowed the analysis of both inorganic gases (TC detector) and organics (FID) simultaneously.

Initially, a 4.7 cc bed of the catalyst was used and mesityl oxide was injected into the system with 5% oxygen using a nitrogen diluent gas at a temperature of 200° C. Over a period of about 4 to 5 hours the temperature was raised gradually to 500° C. when the catalyst coked up badly. The catalyst was decoked with 5% oxygen in nitrogen for about 1 hour. Paraxylene was then substituted for the mesityl oxide and was fed to the reactor. Over a period of 3 to 4 hours the temperature was increased from about 200° to 500° C. without oxidation taking place. Then para-cymene was used to replace the paraxylene and the temperature was increased to 600° C. over a period of several hours using a Liquid Space Velocity (LSV)—(Hr$^{-1}$) resulting in a 92% conversion of the paracymene yielding a selectivity of 10% to para methyl-alpha methylstyrene. As soon as oxygen was deleted from the feed, conversion dropped to about 83% and selectivity to paramethyl alpha methylstyrene increased to 90%.

The next day the reactor was started up again except that paraethyltoluene was fed to the reactor with nitrogen for 4 hours at 600° C. using 0.1 LSV (Hr$^{-1}$) and 1000 CSV (Hr$^{-1}$). Periodic samples indicated that the conversion ranged from about 49 to 53.9% with selectivity ranging from 87 to 92% to paravinyltoluene. The next day the paraethyltoluene run was repeated over a period of 8 hours except using a 0.50 LSV. The percent conversion dropped to about 22 to 27% and the selectivity increased to about 92 to 96%. The next day the run was repeated with essentially the same results. The next day ethylbenzene was used in place of the paraethyltoluene using 0.5 LSV (Hr$^{-1}$) and a 600 GSV (Hr$^{-1}$) resulting in percent conversion ranging from about 19 to 38% with selectivity of from 64 to 84% to styrene. During this period the process was permitted to run overnight for 16 hours. The used copper colored catalyst is described below as I-2.

A fresh sample of copper aluminum borate (I-1) was used to replace I-2 and a 3.3 cc catalyst bed was prepared. Cumene and nitrogen diluent was fed to the catalyst for several days varying the conditions as set forth below in Table III. The run numbers refer to various sampling points.

TABLE III

| Sample No. | Temp. (°C.) | LSV (Hr-1) | GSV (Hr-1) | Conversion | Selectivity | Time After Startup |
|---|---|---|---|---|---|---|
| 1 | 600 | 0.50 | 740 | 70.7 | 82.9 | |
| 2 | 650 | 0.96 | 450 | 77.9 | 67.7 | |
| 3 | 550 | 0.14 | 450 | 40.4 | 90.0 | |
| 4 | 650 | 0.14 | 2100 | 91.1 | 75.2 | |
| 5 | 650 | 0.96 | 2100 | 77.4 | 74.2 | |
| 6 | 600 | 0.50 | 740 | 56.9 | 84.3 | |
| 7 | 550 | 0.14 | 2300 | 27.7 | 81.6 | |
| 8 | 550 | 0.96 | 2300 | 9.9 | 83.4 | |
| 9 | 550 | 0.96 | 500 | 19.8 | 74.5 | |
| 10 | 650 | 0.14 | 400 | 80.0 | 68.9 | |
| 11 | 600 | 0.50 | 740 | 56.5 | 85.1 | |
| 12 | | | | 42.9 | 90.0 | 9 hrs. |
| 12A | | | | 44.8 | 89.7 | 24 hrs. |
| 13 | 600 | 0.50 | 740 | 54.6 | 84.7 | |
| 14 | 600 | 1.37 | 700 | 41.3 | 82.6 | |
| 15 | 675 | 0.50 | 700 | 79.5 | 65.4 | |
| 16 | 525 | 0.50 | 700 | 10.2 | 93.7 | |
| 17 | 600 | 0.50 | 740 | 51.6 | 86.3 | |
| 18 | 600 | 0.10 | 700 | 75.9 | 87.3 | |
| 19 | 600 | 0.50 | 3100 | Data lost | | |

TABLE III-continued

| Sample No. | Temp. (°C.) | LSV (Hr-1) | GSV (Hr-1) | Conversion | Selectivity | Time After Startup |
|---|---|---|---|---|---|---|
| | | | | | due to valve failure | |
| 20 | 600 | 0.50 | 400 | 64.9 | 75.8 | |
| 21 | 600 | 0.50 | 740 | 51.1 | 84.9 | |
| 22 | | | | 38.1 | 89.8 | 32 hrs. |
| 23 | | | | 39.9 | 89.6 | 48 hrs. |
| 24 | | | | 37.2 | 89.5 | 53 hrs. |
| 25 | | | | 36.8 | 89.0 | 73 hrs. |
| 26 | | | | 36.9 | 88.9 | 74 hrs. |

This procedure was carried out for approximately 6 weeks varying the conditions. The copper colored catalyst at this point (II-3) was removed from the reactor and comprised finely divided copper on aluminum borate. Each of the catalyst samples, copper aluminum borate (I-1) and finely divided copper on aluminum borate (I-2 and I-3), were run under the x-ray diffraction conditions referred to above. The strongest line for the copper aluminum borate was 5.29 and the strongest line for the copper on aluminum borate was 2.09 or 2.08 (the copper metal line). In order to make the data more readily comparable, 5.28 and 5.29 were selected as 100%. The x-ray diffraction patterns of these materials is set forth below in Table IV.

TABLE IV

| dA | I-1 I/I$_o$ | I-2 I/I$_o$ | I-3 I/I$_o$ |
|---|---|---|---|
| 7.46 | 13 | | |
| 5.29 | 100 | 100 | |
| 5.28 | | | 100 |
| 4.99 | 62 | | |
| 4.93 | | 24 | |
| 4.91 | | | 19 |
| 3.73 | 17 | | |
| 3.64 | 9 | | |
| 3.59 | | 12 | 19 |
| 3.35 . | | 12 | |
| 3.34 | 14 | | 26 |
| 2.96 | 11 | | |
| 2.84 | 14 | | |
| 2.78 | | 5 | 8 |
| 2.645 | 77 | | |
| 2.64 | | 44 | 38 |
| 2.61 | 20 | | |
| 2.50 | 21 | | |
| 2.46 | | 26 | 42 |
| 2.26 | 30 | | |
| 2.23 | | 12 | |
| 2.22 | | | 17 |
| 2.16 | 39 | | |
| 2.13 | | 47 | 40 |
| 2.09 | | 586 | |
| 2.08 | | | 563 |
| 2.07 | 34 | | |
| 1.98 | 27 | | |
| 1.97 | | 7 | |
| 1.96 | | | 10 |
| 1.91 | | 7 | 8 |
| 1.86 | 19 | | |
| 1.82 | 24 | | |
| 1.81 | | 222 | 217 |
| 1.76 | 9 | | |
| 1.67 | 31 | | |
| 1.66 | | 16 | 19 |
| 1.59 | 11 | | |
| 1.56 | 10 | | |
| 1.55 | | 15 | 18 |

*2.61 was a shoulder on 2.645

The above data clearly shows that copper aluminum borates are reduced to substantially zero valent copper on a copper aluminum borate support or matrix and that both copper aluminum borate and copper on aluminum borate substrates are excellent dehydrogenation catalysts for alkyl substituted aromatics having at least two carbon atoms in at least one alkyl chain.

EXAMPLE II

|  | $CuCrO_3/CuAB$ | Shell 105 | CuAB |
| --- | --- | --- | --- |
| Temperature | 560–580 | 565–590 | 588–600 |
| Conversion | 45–55 | 45–60 | 40–55 |
| Selectivity | 80–88 | 90 | 85–95 |
| LHSV (v/v) | 0.4–0.9 | 0.5–1.1 | 0.3–0.7 |
| LHSV (w/w) | 0.5–1.0 | 0.4–0.9 | 0.3–0.7 |
| Diluent mole ratio | 2:1–10:1 | 20:1 | 7–13 |
| Time Between Regenerations | >10 days | 3 days new, 1 day used | >10 days |

EXAMPLE III

A hot solution of 26.32 g boric acid in 260 ml distilled water was added to 306.56 g of alumina sol (9.56 wt. % solids) in a blender while mixing. To this was added a solution of 51.40 g copper nitrate $[Cu(NO_3)_2.3H_2O]$ and 15.77 g chrominum acetate $[Cr(C_2H_3O_2)_3.H_2O]$ in 110 ml distilled water. After thorough mixing, 61 ml of conc. ammonium hydroxide were added. Mixing was continued until a smooth and uniform product was obtained. It was spread out to dry for five days and then dried in a vacuum oven at 130° C. A portion of the vacuum-dried product was calcined at 765° C. (III-1). Assuming no chromium is incorporated in the copper aluminum borate structure and the chromium is completely converted to copper chromite, the final preparation contains 11.2 wt. % $CuCr_2O_4$. X-ray diffraction indicated that substantially all chromium was converted to copper chromite.

EXAMPLE IV

This example illustrates the dehydrogenation of cumene to alphamethylstyrene using as a catalyst the copper aluminum borate of Example II, the copper aluminum borate/copper chromite of Example III and a commercial iron oxide dehydrogenation catalyst used for the conversion of cumene to alphamethylstyrene. A dehydrogenation reactor was employed in the manner described in Example I using approximately 3.7 cc's of 18–40 mesh catalyst. Cumene, and if used, water were fed into a preheater via a syringe pump and the vapors were combined with nitrogen as a carrier gas and passed over the catalyst. Regeneration, if carried out, was accomplished with a feed comprising 5% oxygen and nitrogen. All lines were maintained at 160° to 180° C. and a sample of the reactor effluent was injected directly into a G.C. column for analysis. The results are set forth below in Table V.

The reactions were terminated after approximately 240 hours. Essentially the same results were obtained with the catalyst comprising copper on an aluminum borate support with either nitrogen or steam as a diluent.

TABLE V

|  | $CuCrO_3/CuAB$ | Shell 105 | CuAB |
| --- | --- | --- | --- |
| Temperature | 560–580 | 565–590 | 588–600 |
| Conversion | 45–55 | 45–60 | 40–55 |
| Selectivity | 80–88 | 90 | 85–95 |
| LHSV (v/v) | 0.4–0.9 | 0.5–1.1 | 0.3–0.7 |
| LHSV (w/w) | 0.5–1.0 | 0.4–0.9 | 0.3–0.7 |

TABLE V-continued

|  | $CuCrO_3/CuAB$ | Shell 105 | CuAB |
| --- | --- | --- | --- |
| Diluent mole ratio | 2:1–10:1 | 20:1 | 7–13 |
| Time Between Regenerations | >10 days | 3 days new, 1 day used | >10 days |

EXAMPLE V

This example illustrates the preparation of $K_2O/MoO_3/CeSO_4$ doped copper aluminum borate and the use thereof for dehydrogenation of para-ethyltoluene. Into a blender was placed 79.36 g $K_2CO_3$, 97.22 g $Cu(NO_3)_2 \cdot 2\frac{1}{2}H_2O$, 51.74 g $H_3BO_3$, 177.30 g $Al(NO_3)_3.9H_2O$, and 70 ml of water. The blender was turned on and after the foaming subsided, another 100 ml of water was added, yielding a clear blue solution. Upon standing overnight, concentrated ammonium hydroxide was added in three stages: 40 ml, 55 ml, and 30 ml with stirring. The material gelled after the third addition of concentrated ammonium hydroxide and was dried yielding 480 g of material.

To 20.65 g of the air dried material prepared in the preceding paragraph was added 30 ml of an aqueous solution containing 0.19 g $(NH_4)_6Mo_7O_{24}.4H_2O$ (2% by weight $MoO_3$ based on doped catalyst) and 50 ml of an aqueous solution containing 0.282 g $Ce_2(SO_4)_6$ of $0.8H_2O$ (about 2% by weight Ce based on doped catalyst). The mixture was stirred intermittently and allowed to air dry. The solid residue was heated to 800° C. over 5 hours, held at 800° C. for 1 hr and allowed to cool down overnight in the oven.

The doped copper aluminum borate catalyst prepared in the preceding paragraph was ground to 18 to 40 mesh and used in the dehydrogenation of ethylbenzene and p-ethyltoluene in the manner described in Example I. The ethylbenzene runs were carried out at a 0.9 liquid hourly space velocity, 620° C. temperature, steam:ethylbenzene ratio of 20:1 yielding 42% conversion and 72% selectivity to styrene. The p-ethyltoluene conversion to p-methylstyrene was carried out using a 0.2 liquid hourly space velocity, 620° C. temperature, 15:1 molar ratio of steam to p-ethyltoluene, a 5:1 toluene to pethyltoluene dilution yielding 68% conversion and 93% selectivity to p-methylstyrene.

EXAMPLE VI

This example illustrates the dehydrogenation of cumene and p-ethyltoluene using a diluent comprising steam and nitrogen. Three and three-tenths of the catalyst prepared in Example I, ground to 18 to 40 mesh, was employed in the reactor described in Example I. Initially p-ethyltoluene was flowed into the reactor at 0.38 liquid hourly space velocity, 11:1 diluent to p-ethyltoluene ratio (8:1 steam and 3:1 nitrogen) at 588° C. yielding a relatively poor conversion and selectivity. The catalyst was decoked with 5% oxygen and nitrogen for about 1 hr. Cumene was then run at 0.38 liquid hourly space velocity, 11:1 diluent ratio (8:1 steam and 3:1 nitrogen) at 588° C. providing 40% conversion to alphamethylstyrene and 88% selectivity. The feed was then switched from cumene to p-ethyltoluene using the same diluent dilution and conditions providing 22% conversion to p-methylstyrene and 93% selectivity. Conditions were then changed to 0.72 liquid hourly space velocity, 10:1 diluent ratio for the p-ethyltoluene (8:1 steam and 2:1 nitrogen) at 598° C. yielding 40% conversion and 92% selectivity to p-methylstyrene.

EXAMPLE VII

This example illustrates conversion of cumene to alphamethylstyrene using a 20:1 diluent ratio and a copper aluminum borate catalyst having a BET surface area of 32 square meters per gram, 0.198 cc per gram pore volume and 98Å average pore radius. The catalyst was prepared in the same manner as the catalyst prepared in Example I except that the concentration of concentrated ammonium and hydroxide was reduced from 60 to 30 ml. After the catalyst was ground to 18 to 40 mesh, 3.85 g (3.8 cc) was placed in the reactor. The dehydrogenation was run using a 20:1 diluent ratio (17:1 steam and 3:1 nitrogen) at 0.81 liquid hourly space velocity at 600° C. yielding 46% conversion and 92% selectivity to alphamethylstyrene.

EXAMPLE VIII

This example illustrates the preparation of a copper aluminum borate/copper chromite catalyst and the use thereof in the dehydrogenation of p-cymene, p-ethyltoluene and cumene. Into a blender was placed 300.77 g of an alumina sol (9.73 dry wt. % $Al_2O_3$, 0.2869 moles $Al_2O_3$) and 23.64 g boric acid (0.38 moles) dissolved in 250 ml of water. A copper nitrate/chromium acetate solution was prepared by dissolving 53.34 g copper nitrate (0.22 moles) in 60 ml water and adding thereto a solution of 15.56 g chromium acetate in 70 ml distilled water. On heating, the copper nitrate/chromium acetate solution became dark and opaque. The dark opaque solution was added to the blender and thoroughly mixed before transfer to petri dishes to dry. The petri dishes were placed in a vacuum oven and dried overnight at 55° C. at 20 inches (0.3 atm) vacuum. Over the next two days, the temperature was gradually raised to 106° C. while the vacuum pressure was increased to about 15 inches (0.5 atm), yielding 110.67 g of a dark blue solid. A portion of this material (27.09 g) was placed in a petri dish and calcined by heating as follows: 120° C. for 0.6 hr, 235° C. for 0.5 hr, 250° C. for 0.5 hrs, 375° C. for 0.8 hr, and then 400° C. After cooling for 1 hr the composition while still at 300° C. was placed in a desiccator overnight. The solid (13.76 g) was placed in a small alumina dish and calcined according to the following program: 40° C. for 2 hrs, 500° C. for 1 hr, 500° C. for 1.5 hrs, 735° C. for 3 hrs and then held at 750° C. and cooled. After cooling for 1.2 hrs, the temperature reached 482° C. and the dish was removed from the oven and placed in a desiccator, yielding 13.48 g of 11.2% copper chromite in copper aluminum borate.

After grinding to 18 to 40 mesh, 3.7 g of the catalyst prepared in the preceding paragraph was placed in a reactor and used in dehydrogenation in the manner described in Example I. The p-cymene runs were carried out at a 0.45 liquid hour space velocity, 592° C. temperature, a steam: p-cymene mole ratio of 20:1, yielding 37% conversion and 31% selectivity. The p-ethyltoluene conversion was carried out using a 0.45 liquid hour space velocity, 588° C. temperature, 15:1 molar ratio of steam to p-ethyltoluene, yielding 32% conversion and 40% selectivity. The cumene conversion was carried out using a 0.94 liquid hour space velocity, 560° C. temperature, a 6:1 molar ratio of diluent to cumene (4:1 steam and 2:1 nitrogen), yielding 47% conversion and 87% selectivity.

EXAMPLE IX

This example illustrates the preparation of a copper oxide on aluminum borate substrate and the in situ conversion of the copper oxide to copper in the dehydrogenation of a cumene. Nine grams of aluminum borate ($Al_4B_2O_9$) was placed into an evaporating dish. One and thirty-nine hundredths grams copper nitrate was dissolved in 6 ml water. The copper nitrate solution was added to the aluminum borate solid until about 4.8 ml solution was absorbed by the solid. The weighed solid was placed in a vacuum oven and the temperature gradually raised to 90° C. The solid was impregnated three additional times with 4.55 ml copper nitrate solution, dried at 97° C., 4.65 ml copper nitrate solution, dried at 98° C. and finally 4.5 ml copper nitrate solution, dried at 106° C., yielding a solid weighing 9.69 g. The resulting solid was placed in an alumina dish and calcined as follows: 120° C. for 1.2 hrs, 275° C. for 0.5 hr, 300° C. for 0.8 hr, 560° C. for 1.0 hr, held at 575° C. and then allowed to cool overnight in a desiccator. The solid weighed 9.31 g and was pressed into two large pellets weighing 4.38 g and 4.34 g respectively.

After grinding to 18 to 40 mesh, 1.938 g of the catalyst (3.0 cc) was placed in the reactor described in Example I. The reactor was heated at 670° C. with 50 cc of air flowing over it overnight. The temperature was reduced to 586° C. and after several hours cumene was introduced at a 0.78 liquid hour space velocity, 7.6 moles of steam per mole of cumene, and 2.0 moles of nitrogen per mole of cumene. Conversion to alphamethyl styrene is set forth in the table below:

TABLE

| Hours On Stream | Percent Conversion | Percent Selectivity |
|---|---|---|
| 3.0 | 64.6 | 85.1 |
| 4.0 | 53.0 | 86.2 |
| 19.0 | 47.8 | 74.1 |
| 42.0 | 45.8 | 78.6 |
| 51.0 | 55.7 | 81.7 |
| 67.0 | 49.5 | 83.8 |
| 68.0 | 50.7 | 82.8 |
| 91.0 | 50.0 | 85.0 |
| 94.5 | 54.5 | 81.7 |
| 95.0 | 52.5 | 83.0 |
| 108.0 | 69.4 | 78.4 |
| 114.0 | 50.5 | 83.8 |
| 131.5 | 51.9 | 78.6 |
| 135.3 | 49.2 | 82.5 |

EXAMPLE X

This example illustrates that in the absence of copper, aluminum borate ($Al_4B_2O_9$) is a poor dehydrogenation catalyst. The dehydrogenation run described in Example I was repeated using 3.0 cc ground aluminum borate, a liquid hour space velocity of 0.78, a diluent ratio of 10:1 (2:1 nitrogen and 8:1 water) at a temperature of 586° C. Initially the conversion started off high at 97% after three hours but there was only 8% selectivity to methylstyrene. After 65 hours, the conversion dropped to 38% and the selectivity rose to 64%. A repeat run yielded essentially the same results.

EXAMPLE XI

This example illustrates the dehydrogenation of cumene to alphamethyl-styrene using the copper (80) zinc (20) aluminum borate. Three and two-tenths cc of the catalyst was placed in the reactor of Example I and the dehydrogenation was run in the same manner using a liquid hour space velocity of 0.88, a diluent ratio of 15:1 (8:1 nitrogen and 7:1 steam) at a temperature of 600° C. The conversion to methylstyrene was approximately 40-45 wt. % and the selectivity was 88-90% but the material was much lighter (nearly colorless) as opposed to the yellow color of other cumene dehydrogenations described above. The copper (80) zinc (20) aluminum borate used above was prepared as follows: A hot solution of 23.05 g boric acid in 240 ml distilled water was added to 310.94 g alumina sol (28.52 g dry solids basis) in a blender while mixing. To this were added 39.95 g copper nitrate and 11.07 g zinc nitrate in 50 ml distilled water. Concentrated ammonium hydroxide (60 cc) was then added and the mixture blended using a spatula until it was very smooth. The gel was placed on a tray and allowed to dry in air for 48 hrs and then dried under vacuum at 91° C. A portion of this solid was calcined at 380° C. to decompose nitrate and then at 825° C. for 3 hrs. The copper (90) zinc (20) aluminum borate was highly crystalline and X-ray diffraction indicated that it was homogeneous. The material had a surface area of 33 square meters per gram, 0.1355 cc/g pore volume and an average pore radius of 59Å.

EXAMPLE XII

This example illustrates the preparation of a large batch of copper aluminum borate and its use in larger scale dehydrogenation reactors using feeds simulating those emanating from an ethylene alkylation of toluene unit. The copper aluminum borate was prepared by (1) adding 400 g $H_3BO_3$ to 3384 ml distilled water and heating to dissolve;

(2) adding 646.4 g $Cu(OAc)_2.H_2O$ to 2400 ml water. Heating and stirring to substantially dissolve. After −15 minutes of heating adding one-half (480 ml) 29% aqueous $NH_3$ to speed dissolution of salt;

(3) weighing 6352 g PHF alumina (7.8% solids) to mixer bowl;

(4) adding hot boric acid solution to the PHF alumina in a mixer. Mixing slowly for 1 minute;

(5) adding remaining 480 ml (29% aqueous ammonium hydroxide) ammonia to $Cu(OAC)_2$ solution.

(6) After all solids were dissolved adding the ammoniacal copper acetate solution to the slowly mixing liquid in the blender forming a gel. Increasing the mixing speed and thoroughly mixing the gel for −5 minutes;

(7) removing the smooth uniform consistency gel from the mixer, and spreading to dry on large plastic sheets in layer −⅛" thick, for two days;

(8) collecting the air-dried catalyst (now shriveled into random sized flakes), placing in crystallizing dishes and loading into a vacuum oven under 20" of house vacuum (maintained with $N_2$ bleed) at 45° C. overnight;

(9) raising the vacuum oven temperature 10-20° C. at a time at intervals over a period of two additional days until 100-110° C. is reached;

(10) transferring the vacuum dried catalyst to alumina trays, then placing in a calcining oven at 120° C. Calcination was as follows:

| | |
|---|---|
| 120° C.→ | 2 hrs |
| 300° C. | 2 hrs |
| 300° C.→ | 3 hrs |
| 820° C. | 3 hrs |
| 820° C.→ | >4 hrs |

Eighty cc of the catalyst (18 to 40 mesh) was placed in a large reactor and a feed comprising 92% toluene, 5.8% p-ethyltoluene, 0.8% ethylene and minor amounts of benzene and metaethyltoluene were fed to the reactor at a weight hour space velocity of 0.16 based on the p-ethyltoluene concentration using a diluent ratio of approximately 16:1 based on the p-ethyltoluene (toluene and ethylene diluents) at 1 atm at 630° C. Over a five day period the average conversion of p-ethyltoluene was 29 to 32% with 80% selectivity to p-ethylstyrene.

This procedure was repeated using a larger reactor containing 256 g catalyst and nitrogen as an additional diluent. In this case the feed contained about 9 wt. % p-ethyltoluene. Conversion was carried out using a weight hour space velocity of 0.04 based on p-ethyltoluene, a 45:1 diluent ratio, and 1 atm pressure at 630° C. Over several days the average conversion was 40 to 45% with 90 to 95% selectivity of the p-ethyltoluene to p-methylstyrene.

EXAMPLE XIII

This example illustrates the production of a catalyst comprising copper aluminum borate/aluminum borate, for use in dehydrogenation and onstream doping using potassium carbonate. To 225.12 g of $Al(NO_3)_3.9H_2O$ in a 1 liter beaker was added 400 ml distilled water while heating on a hot plate, followed by 22.69 g boric acid and 32.21 g copper nitrate. After the solids dissolved, 61.4 ml concentrated ammonium hydroxide was added raising the pH from 0.2 to 2.5 followed by 115 ml 1:1 concentrated ammonium hydroxide:distilled water raising the pH to 3.4. The mixture set up into a thick gel and allowed to stand overnight. The gel was then spread over three plastic dishes and left to dry in the hood for one week. The solids were then dried in three petri dishes in a vacuum oven for 28 hrs at about 20 inches mercury (0.3 atm pressure). The temperature was gradually raised from room temperature to 77° C. after 4 hrs, 105° C. after 8 hrs, 118° C. after 23 hrs and 136° C. at the end of the 28 hr drying period yielding 207.82 g. The copper aluminum borate/aluminum borate mixture was calcined by heating to 400° C. and then at 750° C. (780° C. observed temperature). The copper aluminum borate/aluminum borate had a BET surface area of 109 square meters per gram, 0.3382 cc per g pore volume and an average pore radius of 47 A. XRD pattern showed both copper aluminum borate and aluminum borate ($2Al_2O_3.B_2O_3$) with the ratio of the 5.3 A to 4.95 A lines being 2.9 although the nominal ratios of reactants indicated that the ratio should be 3.9.

The copper aluminum borate/aluminum borate composition was loaded into a reactor and used in dehydrogenation in the manner described in Example I using 2.9 cc catalyst, 1.8 g. The reaction was run at 580° C., a liquid hour space velocity of 0.81, a mole ratio of steam to cumene of 7.6 and a mole ratio of nitrogen to cumene of 2.0. After 45 hrs on stream the percent conversion dropped from about 71.3% conversion to 46.4% conversion and the selectivity increased from 86.3% to 91.8%. At this point there was a brief temperature runaway with the reactor temperature going to 800° to 850° C., for a short time. When the reactor cooled to 580° C. cumene was again started using the same conditions. During the 24 hr period running from 51 hrs on stream to 75 hrs on stream the percent conversion was substantially lower than the earlier part of the run and was approximately 20.1 to 24.5% with 67.7 to 77.7% selectivity. In order to attain improved yields, the catalyst was decoked by adding 161 cc per minute of 7.6% oxygen in nitrogen over the catalyst (no cumene or steam) for 2 hrs at 580° C. Cumene feed was restarted and over the next 48 hrs the percent conversion ranged from about 43.7% to 68.8% with selectivities increase from 44.9% to 92.9%. After 52 hrs on stream, 0.1 cc of a solution of 2 cc water and 1 g potassium carbonate was injected into the top of the catalyst bed and cumene dehydrogenation was resumed under the same conditions. Over the next 14 hrs the percent conversion was maintained at 46.6 to 47.8% with selectivity at 38.3 to 90%. Since the cumene feed was free of ethylbenzene, the addition of potassium carbonate did not seem to have any effect.

At this point dehydrogenation of ethylbenzene was started using the reactor temperature of 600° C., 0.81 liquid hour space velocity, 6.6:1 steam to ethylbenzene ratio and 1.7:1 nitrogen to ethylbenzene ratio. An injection of 0.1 cc of a 50 wt. % solution of potassium carbonate was added 34 hrs after the beginning of this run. The results are set forth below in Table VI.

TABLE VI

| Time (hrs) | % Conversion | % Selectivity |
|---|---|---|
| 1 | 18 | 93 |
| 3 | 24 | 93 |
| 4 | 28 | 72 |
| 5 | 28 | 85 |
| 6 | 31 | 88 |
| 7 | 75 | 81 |
| 8 | 79 | 89 |
| 11 | 82 | 73 |
| 15 | 85 | 64 |
| 16 | 77 | 80 |
| 27 | 63 | 62 |
| 28 | 61 | 64 |
| 32 | 44 | 63 |
| 33 | 57 | 52 |
| 35 | 44 | 61 |
| 38.5 | 38 | 63 |
| 39 | 44 | 61 |
| 51 | 44 | 53 |

TABLE VI-continued

| Time (hrs) | % Conversion | % Selectivity |
|---|---|---|
| 52 | 41 | 61 |

The above table illustrates that the percent conversion rose dramatically over several hours and was nearly 80% with over 85% selectivity at one point, whereas when ethylbenzene was passed over regular copper aluminum borate without potassium doping there was only minimal conversion (10% conversion at 600° C., 0.83 liquid hour space velocity, 7:1 diluent ratio).

What is claimed is:

1. A method of dehydrogenating an alkylaromatic compound containing at least two carbon atoms in at least one alkyl group to an alkenylaromatic which comprises contacting the alkylaromatic with a catalyst comprising copper on a support comprising aluminum borate.

2. The process of claim 1, wherein the alkylaromatic is contacted with the catalyst at a temperature of about 400° to 700° C.

3. The process of claim 2, wherein said dehydrogenation is carried out under vapor phase conditions and the alkylaromatic comprises from 4 to 25 volume percent of the gaseous composition.

4. The Process of claim 3, wherein the gaseous material comprises at least one compound selected from the group consisting of nitrogen, steam, alkyls of from 1 to 10 carbon atoms, benzene and toluene.

5. The process of claim 1, wherein the catalyst comprises copper on an $Al_2B_4O_9$.

6. The process of claim 1, wherein the aluminum borate support comprises copper aluminum borate.

7. The process of claim 1, wherein the catalyst comprises finely divided copper on an aluminum borate support prepared by the reduction of copper aluminum borate.

8. The process of claim 7, wherein the finely divided copper on an aluminum borate support is formed in situ.

9. The process of claim 1, wherein the alkyl aromatic comprises ethylbenzene.

10. The process of claim 1, wherein the alkyl aromatic comprises cumene.

11. The process of claim 1, wherein the alkyl aromatic comprises paraethyltoluene.

12. The process of claim 1, wherein the alkyl aromatic comprises p-cymene.

* * * * *